United States Patent
Godshall et al.

Patent Number: 5,879,326
Date of Patent: Mar. 9, 1999

[54] METHOD AND APPARATUS FOR DISRUPTION OF THE EPIDERMIS

[76] Inventors: Ned Allen Godshall, 1105 Rocky Point Ct. NE, Albuquerque, N. Mex. 87123; R. Rox Anderson, 399 Marrett Rd., Lexington, Mass. 02173

[21] Appl. No.: 845,627

[22] Filed: Apr. 25, 1997

Related U.S. Application Data

[63] Continuation-in-part of Ser. No. 445,704, May 22, 1995, abandoned.

[51] Int. Cl.⁶ .................................................. A61M 31/00
[52] U.S. Cl. ................................ 604/51; 604/49; 604/46; 606/186
[58] Field of Search ................................. 604/46, 47, 48, 604/49, 51, 117, 181, 289, 290, 890.1

[56] References Cited

U.S. PATENT DOCUMENTS 3,964,482  6/1976  Gerstel et al. ........................... 128/260

Primary Examiner—Wynn Wood Coggins
Assistant Examiner—Deborah Blyveis
Attorney, Agent, or Firm—Calvin B. Ward

[57] ABSTRACT

A method and apparatus for mechanically disrupting a layer of skin having a known thickness without substantially disrupting underlying dermis layers below the layer of skin in question so as to facilitate the delivery of compounds across the disrupted layer. The apparatus includes a cutter having a plurality of microprotrusions having a height chosen with respect to the layer of skin that is to be disrupted and a stop for preventing the apparatus from penetrating the skin beyond a predetermined distance. In the preferred embodiment of the present invention, the microprotrusions include blades that generate cuts in the layer of skin. The cuts are generated by moving the apparatus parallel to the surface of the skin either at the time of application, during the normal movements of the individual wearing the apparatus, or both. In the preferred embodiment of the present invention, the appropriate length of blade is determined for each individual and delivery site on that individual.

8 Claims, 2 Drawing Sheets

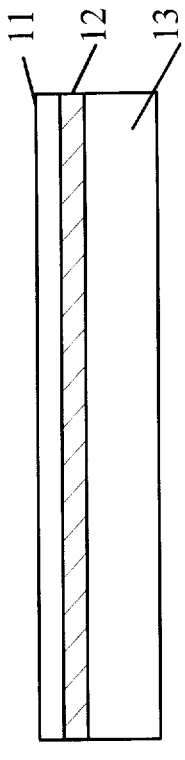
FIGURE 2
FIGURE 3
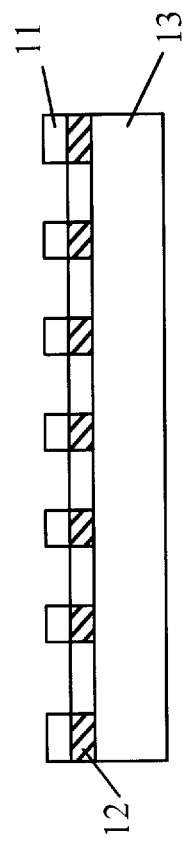
FIGURE 4
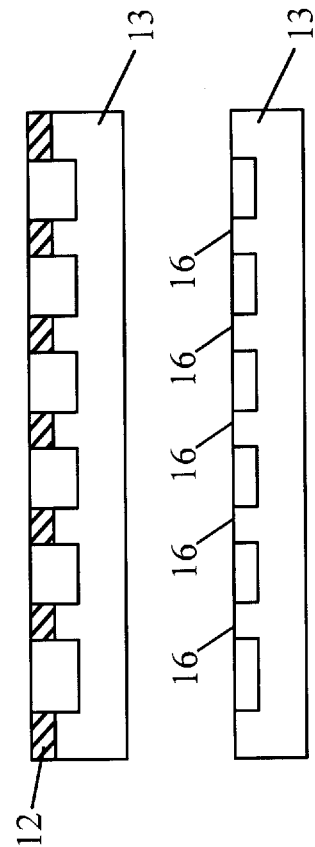
FIGURE 5
FIGURE 6
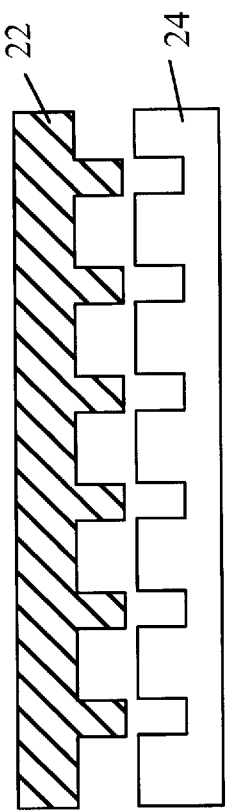

METHOD AND APPARATUS FOR DISRUPTION OF THE EPIDERMIS

RELATED APPLICATIONS

This application is a Continuation-in-Part of U.S. patent application Ser. No. 08/445,704, filed May, 22, 1995, now abandoned.

FIELD OF THE INVENTION

The present invention relates to drug delivery systems, and more particularly, to a mechanical device that alters the outermost layer of skin to greatly improve the delivery of compounds through the skin.

BACKGROUND OF THE INVENTION

Transdermal delivery of medication is well known in the prior art. Transdermal patches are available for a number of drugs. Commercially available examples of transdermal patches include scopolamine for the prevention of motion sickness, nicotine for aid in smoking cessation, nitroglycerin for the treatment of coronary angina pain, and estrogen for hormonal replacement. Generally, these systems have drug reservoirs sandwiched between an impervious backing and a membrane face which controls the steady state rate of drug delivery. The systems usually are attached to the skin by an adhesive gel with the membrane face adjacent to the skin.

Transdermal medication has significant advantages over both hypodermic injection and oral administration. A transdermal patch can provide significantly greater effective blood levels of a beneficial drug because the drug is not delivered in spike concentrations as is the case with hypodermic injection and most oral administration. In addition, drugs administered via transdermal patches are not subjected to the harsh environment of the digestive tract. Hence, in principle, transdermal delivery provides a method for administrating drugs that would otherwise need to be administered via hypodermic injection or intravenous infusion because the drug is destroyed in the digestive tract or immediately absorbed by the liver. Conversely, the digestive tract and liver are not subjected to the drug in transdermal administration. Many drugs, such as aspirin, have an adverse effect on the digestive tract.

Prior art transdermal drug delivery systems may be divided into passive diffusion and active transport systems. Transdermal drug delivery by diffusion is by far the most common of the transdermal methods. The nicotine patch is an example of this method of delivery (U.S. Pat. No. 4,597,961 to Frank T. Etscorn). This process is based on presenting the medication in a high dose external to the dermis and allowing the chemical to diffuse into and through the skin. The degree of diffusion depends on the porosity of the skin, the size and polarity of the drug molecules, and the concentration gradient across the stratum corneum, the outermost layer of human skin. These factors generally limit this mode of delivery to a very small number of useful drugs with very small molecules or unique electrical characteristics.

There have been two types of systems proposed to overcome the limited range of compounds that may be administered transdermally. The first class of techniques are based on the disruption of the skin to remove the diffusion barrier. One such method is described in U.S. Pat. No. 3,964,482. This technique utilizes an array of needle like protrusions that penetrate the stratum corneum. The drug is delivered either through the needles or on the surface of the skin. In the this case, the drug flows along the outer surface of the "needle" through the hole in the stratum corneum created by the needle. The length of the needles utilized in this invention is just long enough to penetrate the stratum corneum. Since the stratum corneum does not contain blood vessels or nerve endings, the patient does not experience bleeding or discomfort from the penetration of the needles.

The second class of drug delivery system involve the active transport of the compounds across the skin. The active diffusion systems involve iontophoresis, electroporation and ultrasound to increase the migration of the drug across the skin barrier. These methods attempt to electrically assist diffusion of the medication or apply high frequency electrical pulses or sound waves to the skin to improve absorption. Unfortunately, the high cost and inconvenience of providing portable electrical equipment have limited the commercial application of such active systems.

While this device has been known for over 25 years, devices of this type have not been commercially successful. The disruption of the stratum corneum is not sufficient to render the skin sufficiently permeable to allow many compounds of interest to be administered transdermally. In addition, the disruption provided by beds of "needles" and the like does not permit reproducible drug flow across the disrupted area. The needles used to make the holes fill the holes, thus blocking drug delivery. Furthermore, even if the needles are removed, the small holes produced thereby rapidly close on removal of the needle assembly.

Accordingly, it is a general object of the present invention to provide an improved apparatus and method for disrupting the outer skin layers in a manner that permits the layers to become permeable to drugs and the like.

It is another object of the invention to provide a method for disrupting the skin layers such that the disrupted area remains permeable for a time that is sufficient to administer compounds through the skin.

It is another object of the invention to eliminate or greatly reduce the pain of drug delivery by present skin-penetrating devices, such as needles, fluid jets, etc.

It is another object of the present invention to provide a transdermal delivery system that does not rely on applied electric fields, yet allows drugs that could not previously be administered by passive diffusion to be so administered.

These and other objects of the present invention will become apparent to those skilled in the art from the following detailed description of the invention and the accompanying drawings.

SUMMARY OF THE INVENTION

The present invention comprises an apparatus for mechanically disrupting a layer of skin having a known thickness without substantially disrupting underlying dermis layers below the layer of skin in question so as to facilitate the delivery of compounds across the disrupted layer. The apparatus includes a cutter having a plurality of microprotrusions having a height chosen with respect to the layer of skin that is to be disrupted and a stop for preventing the apparatus from penetrating the skin beyond a predetermined distance. In the preferred embodiment of the present invention, the microprotrusions include blades that generate cuts in the layer of skin. The cuts are generated by moving the apparatus parallel to the surface of the skin either at the time of application, during the normal movements of the individual wearing the apparatus, or both. In the preferred embodiment of the present invention, the appropriate length of blade is determined for each individual and delivery site on that individual. After the layer of skin is mechanically disrupted, a drug or other chemical compound may be administered to the patient using conventional creams, ointments, or transdermal patch techniques.

BRIEF DESCRIPTION OF THE DRAWINGS

FIGS. 2–5 are cross-sectional views of a silicon substrate at various stages in the fabrication of a bed of microprotrusions according to the present invention.

FIG. 6 is a cross-sectional view of a mold and a bed of microprotrusions constructed thereon.

DETAILED DESCRIPTION OF THE INVENTION

Figure 1:
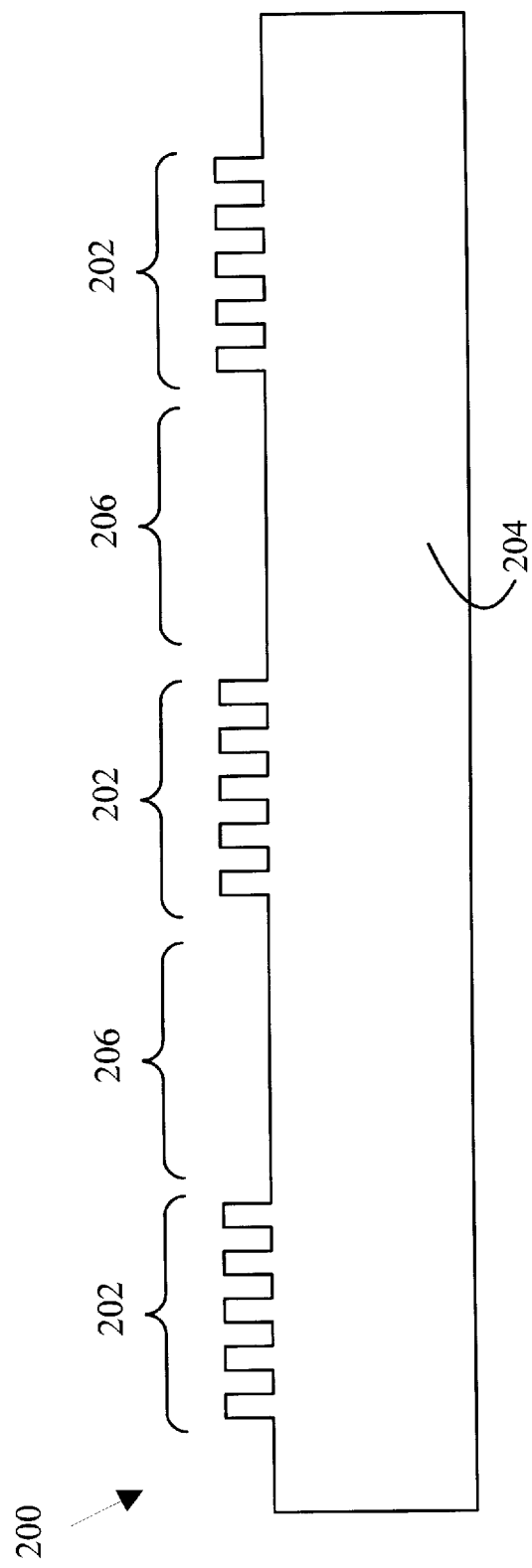
FIG. 1 is a cross-sectional view of a micromechanical device according to the present invention.

The present invention is based on the observation that the the epidermis layer under the stratum corneum is approximately 100 $\mu$m thick, and like the stratum corneum, has substantially no blood vessels or nerve endings. While the epidermis does have live cells that are fed by diffusion from the dermis below, it can be penetrated without bleeding or pain. Hence, a microcutter or bed of "needles" can penetrate through the stratum corneum to a depth of the top of the epidermal/dermal interface folds without causing discomfort or bleeding. It has been found experimentally that devices that disrupt both the stratum corneum and epidermis increase the permeablity of the skin significantly over that obtained by merely disrupting the stratum corneum. The increase in permeability is sufficient to allow clinically significant doses of compounds to be administered that would otherwise not penetrate the skin if only the stratum corneum is penetrated.

The present invention is based on mechanically penetrating or disrupting the stratum corneum and epidermis layers, thereby improving the effectiveness of transdermal delivery of drugs incapable of diffusion through the skin with these layers intact. The simplest embodiment of the present invention comprises a bed of microneedles or microcutters that are just long enough to effectively penetrate the stratum corneum and the epidermis. This bed of microprotrusions can be placed on the skin, and moved horizontally relative to it to generate a large number of microdisruptions in the epidermis and stratum corneum layers. This bed of microprotrusions can be inexpensively manufactured by one of several technologies commonly referred to as micromachining (micromechanics, Micro Electro Mechanical Systems, known as MEMS, etc.).

The problems introduced by the stratum corneum have been recognized for some time. However, the need to also penetrate the epidermis has not been previously appreciated. Techniques that grossly remove both the stratum corneum and epidermis layers, as well as some of the underlying layers are known. For example, techniques in which the epidermis and stratum corneum are removed by placing sticky tape in contact with the skin and then ripping off the tape have been used. Unfortunately, such techniques are painful and, in addition, remove a significant amount of underlying dermis layer. The loss of dermis can result in bleeding and the possibility of infection. Such techniques are impractical for clinical practice, and disrupt the skin such that healing takes a week or longer.

The present invention, however, utilizes a mechanical method for penetrating the stratum corneum and a portion of the epidermis layer without substantially damaging the underlying layers. Hence, blood vessels and nerve endings are not damaged. The simplest embodiment of the present invention is a bed of microcutters 202 attached to a substrate 204 as shown in FIG. 1 which is a cross-sectional view of a skin disrupter 200 according to the present invention. The areas 206 between the groups of microprotrusions also act as a penetration "stop" that prevents the microcutters from penetrating the skin to a depth substantially greater than the height of the microcutters.

The manner in which such a bed of microprotrusions can be constructed is illustrated in FIGS. 2–6. Refer first to FIGS. 2–5 which illustrate one of several methods for the fabrication of a bed of microprotrusions in a silicon substrate 13. A layer 12 of silicon dioxide is first deposited on substrate 13. A layer 11 of photoresist is then deposited on oxide 12 and patterned using conventional photolithography techniques. The patterned photoresist layer is used to control the etching of the oxide layer using a fluorine reactive ion etch process which stops on the silicon. The patterned oxide layer is then used as a mask for a chlorine reactive ion etch that penetrates the silicon substrate leaving protrusions 16. The intermediate oxide masks ensure straight sidewalls and consistent edge depths. Alternatively, the microcutter may be composed of the structure shown in FIG. 3 after the top layer of photoresist 11 is removed, provided the silicon oxide layer 12 is deposited with a thickness approximately equal to the thickness of the stratum corneum/epidermis layers.

Yet another alternative method for generating a bed of microprutrusions is illustrated in FIG. 6 which is a cross-sectional view of a mold 24 used to fabricate, for example, a plastic/polymer microcutter 22. Plastic/polymer structures having features of the same general dimensions as those needed for the microcutter have been demonstrated in polystyrene and polyimide. However, other plastics/polymers such as polycarbonate may be used. The mold may be constructed as described above. However, it will be apparent to those skilled in the art that a number of different methods for constructing a mold with the necessary microstructure may be utilized.

The embodiment of a microcutter according to the present invention is a blade that cuts the skin either when the device is applied or as a result of motion of the device with respect to the skin. Blades have the advantage of being less likely to break during the movement of a microcutter relative to the patient's skin than microneedles. When the device is applied to the patient's skin, it is pressed against the skin and moved laterally in a direction parallel to the surface of the skin, thereby introducing a number of small shallow microcuts. Drugs may then be placed on the skin in the form of a patch, gel, cream, or ointment.

As noted above, the microcutter must be designed so as to disrupt at least the stratum corneum and upper epidermal layers without interrupting the dermis. The length of the microprotrusions will determine the depth of the cut; however, the precise length needed for any given patient may vary from patient to patient because of differences in the thickness of the stratum corneum and upper epidermal layers between patients and other surface characteristics of the patient's skin.

In general, the recipient's skin is not a smooth surface. It contains "hills" and "valleys". In addition, the thickness of the stratum corneum varies from person to person and from place to place on any given person's body. The stratum corneum on the forearm, for example, is typically much thinner than the stratum corneum layer on the heel or the hand. It has been found experimentally that a microcutter having blades with lengths between 50 µm and 175 µm is acceptable for a significant fraction of the population if the device is applied to the forearm. At lengths significantly greater than 175 µm, the patient feels pain when the device is applied to the forearm and moved laterally across the skin to make the incisions. Blade lengths of less than 50 µm do not result in microcuts that extend through the stratum corneum and into the epidermis sufficiently to provide the required degree of diffusion for the compound being applied.

One method for dealing with the variation in thickness of these layers is to measure the thickness of these layers for each patient at the intended place of application of the patch. A series of microcutter's having different length blades can be used for this purpose.

If the blade is too short, the stratum corneum will not be penetrated. A dye such as Coomassie Blue can be used to determine when the stratum corneum has been penetrated, since this dye does not stain the stratum corneum but does stain the underlying epidermis layer. Hence, the application of the dye to the microscratch generated by the microcutter will stain the microscratch if the stratum corneum was penetrated. The depth of the stratum corneum can be determined by noting the shortest length microcutter that causes the microscratch to appear stained by the dye. The depth of the epidermis can be determined by observing the length of microcutter which causes the patient to feel pain when the microcutter is moved laterally across the skin. The optimum length of the microcutters is between these two limits. Experimentally, it has been found that painless, bloodless transcutaneous drug delivery is greatly enhanced by microdisruptions of the interface between the stratum corneum and the epidermis, and particularly, to a depth in the epidermis just above the top of the folds of the epidermis/dermis interface.

It should be noted that the Coomassie Blue dye mentioned above can also be used to determine the minimum length blade needed to disrupt the skin to increase diffusion sufficiently to administer a compound transdermally. It has been observed experimentally that Coomassie Blue will cause a stinging sensation when the microcut penetrates a substantial distance into the epidermis. This stinging sensation results from the dye diffusing into the dermis where it interacts with the nerve endings that are in the dermis. Hence, the optimal length of the microcutter blades can be determined by using a series of microcutter blade lengths and observing whether or not the patient feels a stinging sensation within a few seconds of the application of the dye. A blade length which is less than that which causes pain without the dye, but greater than that which causes pain with the application of the dye has been found to be optimal for the purposes of facilitating the delivery of compounds through the skin.

While the above-described fabrication techniques utilized silicon substrates to form the microprotrusions directly or through molding of plastics/polymers, metals or the like, it will be apparent to those skilled in the art from the above discussion that microprotrusions may be fabricated as an inexpensive and identical array of microblades by any one of several technologies known as micromachining, micromechanics, MEMS, or microfabrication techniques. These microelectronic-like technologies typically first employ the deposition onto a substrate of various films on the size scale of the stratum corneum thickness. Examples of typical films include silicon nitride, silicon oxide, polyimide, aluminum, gold, etc. Secondly, a photolithography technique imparts an image of an array of hundreds or thousands of tiny structures to the top film layer. After selective etching, this results in the fabrication of millions of identical microstructures on the size scale of the stratum corneum thickness. Other process steps include wet etching, plasma etching, or reactive ion etching a photosensitive polymer film (resist) on a silicon substrate or wafer as is common in the microelectronics industry. The films may be deposited by chemical vapor deposition techniques prior to the etching operation. The substrate is then bulk and/or surfaced micromachined to achieve the required height.

Various modifications to the present invention will become apparent to those skilled in the art from the foregoing description and accompanying drawings. Accordingly, the present invention is to be limited solely by the scope of the following claims.

What is claimed is:

1. A method for transdermal delivery of a compound to an animal at a site on that animal's skin, said skin comprising a stratum corneum layer, an epidermis under said stratum corneum, and a dermis layer under said epidermis, said method comprising the steps of:

determining a depth of a cut that will extend through the stratum corneum of that animal at said delivery site but not penetrate the dermis of that animal at said delivery site; and applying an apparatus at said delivery site to generate a cut extending through said stratum corneum layer, said cut extending into said epidermis but not into said dermis layer, said apparatus comprising:

a plurality of microprotrusions for disrupting the skin at said delivery site, said mircoprotrusions having a length determined by said determined depth;

stop means for preventing said apparatus from penetrating said layer of skin beyond a predetermined distance; and applying said compound to said delivery site.

2. The method of claim 1, wherein at least one of said microprotrusions is a blade having an elongated cross-section, said blade being positioned so as to cut said layer of skin when said apparatus is moved relative to said layer of skin, and wherein said step of applying said apparatus comprises moving said apparatus across said layer of skin so as to induce a microcut in said layer skin.

3. The method of claim 1 wherein said step of determining depth comprises the steps of:

moving an apparatus having a microprotrusion of a fixed length and a stop means for preventing said microprotrusion from penetrating the animal to a depth greater than said fixed length, said moving of said apparatus inducing a microcut in said skin; and determining if said microcut extends into the epidermis of that animal at said delivery site.

4. The method of claim 3 wherein said step of determining if said microcut extends into the epidermis of said animal comprises applying a compound to said microcut; and determining if said compound has entered the epidermis of said animal.

5. The method of claim 1 wherein said microprotrusions comprise molded polymer or metal microprotrusions.

6. The method of claim 1 wherein the step of applying a compound to said delivery site comprises dispensing said compound through a channel in one of said microprotrusions.

7. A method for transdermal delivery of a compound to an animal at a site on that animal's skin, said skin comprising a stratum corneum layer, an epidermis under said stratum corneum, and a dermis layer under said epidermis, said method comprising the steps of:

determining a depth of a cut that will extend through the stratum corneum of that animal at said delivery site but not penetrate the dermis of that animal at said delivery site; and applying an apparatus at said delivery site to generate a cut extending through said stratum corneum layer, said cut extending into said epidermis but not into said dermis layer, said apparatus comprising:

a plurality of microprotrusions for disrupting the skin at said delivery site, said mircoprotrusions having a length determined by said determined depth;

stop means for preventing said apparatus from penetrating said layer of skin beyond a predetermined distance; and applying said compound to said delivery site, wherein said step of determining if said microcut extends into the epidermis of said animal comprising applying a compound to said microcut; and determining if said compound has entered the epidermis of said animal, and wherein said compound comprises a dye.

8. The method of claim 7 wherein said dye is Coomassie Blue.

* * * * *

UNITED STATES PATENT AND TRADEMARK OFFICE
CERTIFICATE OF CORRECTION

PATENT NO : 5,879,326
DATED : 3/9/99
INVENTOR(S) : Godshall, et al.

It is certified that error appears in the above-identified patent and that said Letters Patent is hereby corrected as shown below:

Column 1, line 61: Replace "are" with - - is- - before "based".
Column 1, line 67: Delete "the" (first occurrence)
Column 2, line 7: Replace "involve" with - - involves - - after "system".
Column 6, line 15: Replace "surfaced" with - - surface - -

Claim 2- column 6, line 47: Insert - - of - - between "layer" and "skin".

Signed and Sealed this

Nineteenth Day of October, 1999

Attest:

Attesting Officer

Q. TODD DICKINSON

Acting Commissioner of Patents and Trademarks